US011182459B1

(12) United States Patent
Leonardi

(10) Patent No.: US 11,182,459 B1
(45) Date of Patent: Nov. 23, 2021

(54) AUTOMATED COMPARATIVE HEALTHCARE, FINANCIAL, OPERATIONAL, AND QUALITY OUTCOMES AND PERFORMANCE BENCHMARKING

(71) Applicant: SENTRY DATA SYSTEMS, INC., Deerfield Beach, FL (US)

(72) Inventor: Travis Leonardi, Deerfield Beach, FL (US)

(73) Assignee: SENTRY DATA SYSTEMS, INC., Deerfield Beach, FL (US)

(*) Notice: Subject to any disclaimer, the term of this patent is extended or adjusted under 35 U.S.C. 154(b) by 650 days.

(21) Appl. No.: 14/867,994

(22) Filed: Sep. 28, 2015

Related U.S. Application Data

(60) Provisional application No. 62/056,339, filed on Sep. 26, 2014.

(51) Int. Cl.
*G06F 16/33* (2019.01)
*G06F 16/2457* (2019.01)
(Continued)

(52) U.S. Cl.
CPC ...... *G06F 19/325* (2013.01); *G06F 16/24578* (2019.01); *G06F 16/3334* (2019.01);
(Continued)

(58) Field of Classification Search
CPC .. G06Q 50/22; G06Q 50/24; G06Q 10/06375; G06Q 30/0631; G06Q 10/10; G06Q 30/02
(Continued)

(56) References Cited

U.S. PATENT DOCUMENTS 5,778,345 A * 7/1998 McCartney ............ G16H 40/20
705/2
2002/0023176 A1* 2/2002 Kwicinski .............. G06Q 10/10
719/317
(Continued)

OTHER PUBLICATIONS

Nelson Mazzuchi, Juan M. Fernández-Cean, Enriqueta Carbonell; "Criteria for selection of ESRD treatment modalities," Kidney International, Jan. 2000, vol. 57, Supplement 74, pp. S136-S143 (Year: 2000).*
(Continued)

*Primary Examiner* — Rachel L. Porter
(74) *Attorney, Agent, or Firm* — Loeb & Loeb LLP

(57) ABSTRACT

The example embodiments may relate to retrieving a plurality of cost of care records identifying costs to treat a plurality of patients diagnosed with a particular ailment, wherein each of the cost of care records indicates a cost to treat one of the patients using a selected one of a plurality of treatment modalities, wherein each of the treatment modalities identifies at least one of a drug and a supply item. The example embodiments may further relate to processing the cost of care records for determining at least one factor for each of the treatment modalities, determining a performance index for each of the treatment modalities that is a weighted function of the at least one factor, selecting one of the treatment modalities based on the performance indices, and automatically ordering at least one of a drug and a supply item identified in the selected treatment modality for delivery to a health care provider.

12 Claims, 8 Drawing Sheets

(51) Int. Cl.
  *G16H 20/00* (2018.01)
  *G16H 70/20* (2018.01)
  *G06F 19/00* (2018.01)
  *G16H 50/20* (2018.01)
  *G06F 16/9535* (2019.01)
  *G16H 40/00* (2018.01)
  *G06Q 40/08* (2012.01)

(52) U.S. Cl.
  CPC ........ *G06F 16/9535* (2019.01); *G06F 19/328* (2013.01); *G16H 20/00* (2018.01); *G16H 40/00* (2018.01); *G16H 50/20* (2018.01); *G06Q 40/08* (2013.01); *G16H 70/20* (2018.01)

(58) Field of Classification Search
  USPC ........................................................ 705/2, 3

See application file for complete search history.

(56) References Cited

U.S. PATENT DOCUMENTS

| | | |
|---|---|---|
| 2011/0054935 A1 | 3/2011 | Hardaway |
| 2011/0166883 A1* | 7/2011 | Palmer .................. G06Q 50/24 |
| | | 705/3 |
| 2014/0046682 A1* | 2/2014 | Soto ....................... G06Q 40/08 |
| | | 705/2 |
| 2015/0088541 A1* | 3/2015 | Yao ........................ G16H 20/00 |
| | | 705/2 |
| 2015/0100341 A1* | 4/2015 | Pecora ................. G06F 16/9024 |
| | | 705/2 |
| 2015/0278924 A1 | 10/2015 | Maurer |
| 2016/0034648 A1* | 2/2016 | Mohlenbrock ........ G16H 40/20 |
| | | 705/3 |
| 2016/0035040 A1* | 2/2016 | Young .................... G06Q 40/08 |
| | | 705/4 |

OTHER PUBLICATIONS

Sample 340B Policy & Procedures Manual, Feb. 2014, Apexus, pp. 1-18.

* cited by examiner

PHARMACY
Cost Greater Than Charge Amount — 402

NDC [            ]  Vendor [            ]

Description [            ]  Manufacturer [            ]

Review Period [09/17/2014] to [09/17/2015]

[ Search ]

‹ Previous   Page [1] of 3   Next ›   Show [100 ▼] per page

404

| NDC | Charge Code | Description | Mfr. | On Contract | Account Type | Qty | Dispensation Cost | Charge Amount | Financial Impact |
|---|---|---|---|---|---|---|---|---|---|
| 63323-0269-29 | 19058858 | RXDIPRIVAN USP 10/MG/ML VL 10X20 ML | APP PHARMEACEUTICAL | No | WAC | 307 | $573.60 | $102.00 | $-144,781.20 Resolve » |
| 63323-0269-29 | 19058841 | RXDIPRIVAN USP 10/MG/ML VL 10X20 ML | APP PHARMEACEUTICAL | No | WAC | 307 | $286.80 | $51.00 | $-72,390.60 Resolve » |
| 50242-0134-58 | 19800021 | RXHERCEPTIN 440 MG MDV 1 | GENENTECH | No | 340B | 65 | $873.41 | $17.00 | $-55,666.65 Resolve » |
| 10019-0956-01 | 19311903 | RXCYCLOPHOSPHAMIDE 1 GM VL | BAXTER HEALTHCARE CORPORATION | No | 340B | 128 | $529.56 | $193.00 | $-43,079.68 Resolve » |
| 63323-0269-29 | 19058866 | RXDIPRIVAN USP 10/MG/ML VL 10X20 ML | APP PHARMEACEUTICAL | No | WAC | 307 | $114.72 | $30.00 | $-26,009.04 Resolve » |
| 63323-0269-29 | 19058858 | RXDIPRIVAN USP 10/MG/ML VL 10X20 ML | APP PHARMEACEUTICAL | No | GPO | 212 | $220.30 | $102.00 | $-25,079.60 Resolve » |

406   408   410   412   414

Export to Excel   223 results

FIGURE 4

PHARMACY
View More

Cost Greater Than Charge Amount
RXDIPRIVAN USP 10MG/ML VL 10X20 ML

| | | | |
|---|---|---|---|
| NDC | 63323-0269-29 | Annual Volume | 307 |
| Vendor | AmerisourceBergen | Dispensation Cost | $573.60 |
| Manufacturer | APP PHARMACEUTICAL | Charge Code | 19058858 |
| Ratio | 1 | Charge Amount | $102.00 |

Show Purchases and Utilization

Costs Greater than Charge Amount — 502

You can resolve this issue by doing one of the following:

- 504A — Select an alternative as your primary item going forward (listed below).
- 504B — Update the Charge Amount
- 504C — Ignore for New Discussion/Activity (0)

Alternatives

◄ Previous   Page [1] of 1   Next ▶   Show [100 ▼] per page

| ▼NDC | Map | ▼Description | ▼Strength | ▼Form | Pkg Size | ▼B/G | ▼U.D. | ▼Mfr. | ▼AMU | 340B UOM ▼Price | WAC UOM ▼Price | GPO UOM ▼Price | Last UOM ▼Purchased | ▼GPI | |
|---|---|---|---|---|---|---|---|---|---|---|---|---|---|---|---|
| ☒ 63323-0269-65 | 0 | DIPRIVAN 10 MG/ML 10x100 ML EMUL | 10 MG/ML | EMUL | 10 X 100 | B | No | APP PHARMACEUTICAL | $28.67 | $3.65 | $28.69 | $10.87 | 08/24/2015 | 70-40-00-50-00-16-20 | Select |
| ☒ 63323-0269-65 | 0 | PROPOFOL 10 MG/ML 10x100 ML EMUL | 10 MG/ML | EMUL | 10 X 100 | G | No | HOSPIRA | $0.00 | $11.19 | $11.92 | $11.92 | 03/07/2015 | 70-40-00-50-00-16-20 | Select |

◄ Previous   Page [1] of 1   Next ▶   Show [ ] per page    Package Size: [10 x 100 ▼]   Show All ▼    Filter   Export to Excel   2 results

FIGURE 5

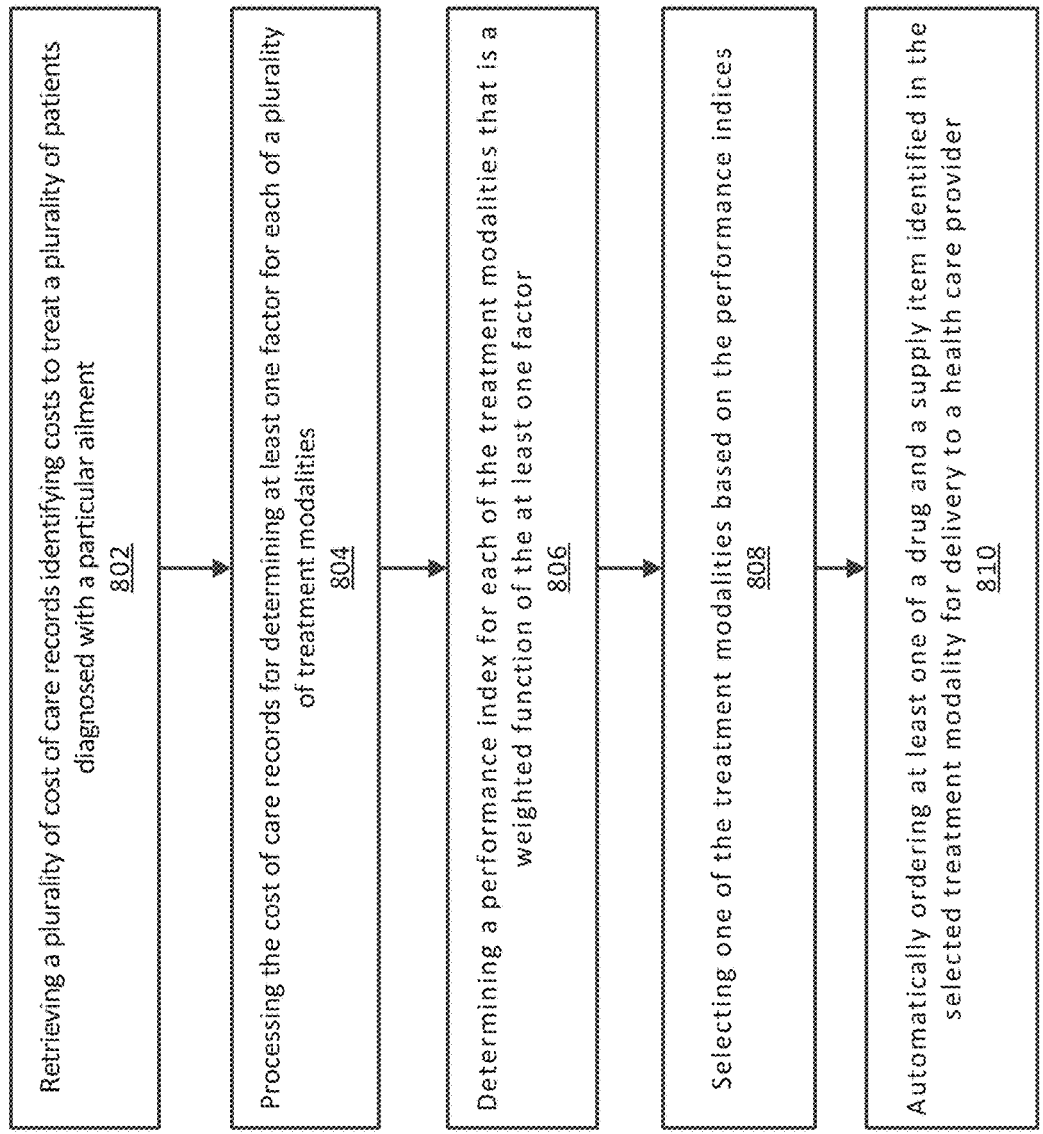

AUTOMATED COMPARATIVE HEALTHCARE, FINANCIAL, OPERATIONAL, AND QUALITY OUTCOMES AND PERFORMANCE BENCHMARKING

CROSS REFERENCE TO RELATED APPLICATIONS

This application claims the benefit of, and priority to, U.S. Prov. Appl. No. 62/056,339 filed Sep. 26, 2014, entitled "Automated Comparative Healthcare, Financial, Operational, And Quality Outcomes And Performance Benchmarking," the entire content of which is incorporated herein by reference.

BACKGROUND

Field of the Invention

The invention relates to systems and methods for outcome and performance benchmarking. Among other fields and applications, the invention has utility in facilitating management of health care facilities.

Description of Related Art

In recent years, private and public health plans have implemented financial incentives and penalties for hospitals that underperform based upon certain quality of care and patient outcome indicators. Hospitals across the country are challenged with improving the quality of care and outcomes of the patient population while simultaneously managing financial performance. During the course of the past 25 years, the healthcare industry has developed a variety of key performance indicators that provide some approximation of the hospital's quality of care performance and overall financial "health". The majority of these key performance indicators are calculated based upon a hospital's submitted Medicare and Medicaid claims. By definition, claims-based hospital ranking systems are limited in the types of comparative analytics they can perform due to the limitations of public databases.

Today, many hospitals are subject to financial penalties for not meeting certain patient quality and outcome performance benchmarks (e.g., 30 day re-admissions, etc.). There are many methods and industry sources of best practices that can assist hospitals with these challenges including several hospital ranking systems that allow for high-level hospital comparisons measuring key financial and other performance indicators. Underlying each of these key financial, operational and clinical metrics are many inputs that are not available in either an identifiable or anonymized form to other hospitals. As a result, an underperforming hospital cannot access specific detailed information about other better performing hospitals that would reveal specific differences across cost, operational, clinical functions that would enable the underperforming hospital to make specific changes that would improve their overall and comparative financial, operational or clinical performance.

BRIEF SUMMARY

The following presents a simplified summary of the present disclosure in order to provide a basic understanding of some aspects of the disclosure. This summary is not an extensive overview of the disclosure. It is not intended to identify key or critical elements of the disclosure or to delineate the scope of the disclosure. The following summary merely presents some concepts of the disclosure in a simplified form as a prelude to the more detailed description provided below.

Example embodiments of a system, apparatus, computer readable media, and method are disclosed to optimize quality of care for a patient. Specifically, the example embodiments may be used for retrieving a plurality of cost of care records identifying costs to treat a plurality of patients diagnosed with a particular ailment, wherein each of the cost of care records indicates a cost to treat one of the patients using a selected one of a plurality of treatment modalities, wherein each of the treatment modalities identifies least one of a drug and a supply item, processing the cost of care records for determining at least one factor for each of the treatment modalities, determining a performance index for each of the treatment modalities that is a weighted function of the at least one factor, selecting one of the treatment modalities based on the performance indices, and automatically ordering at least one of a drug and a supply item identified in the selected treatment modality for delivery to a health care provider.

BRIEF DESCRIPTION OF THE DRAWINGS

The invention may be better understood by references to the detailed description when considered in connection with the accompanying drawings. The components in the figures are not necessarily to scale, emphasis instead being placed upon illustrating the principles of the invention. In the figures, like reference numerals designate corresponding parts throughout the different views.

FIG. 4 illustrate an example issue class GUI in accordance with example embodiments.

FIG. 5 illustrates a resolution GUI in accordance with example embodiments.

FIG. 8 illustrates a flow diagram of a method in accordance with example embodiments.

Figure 1:
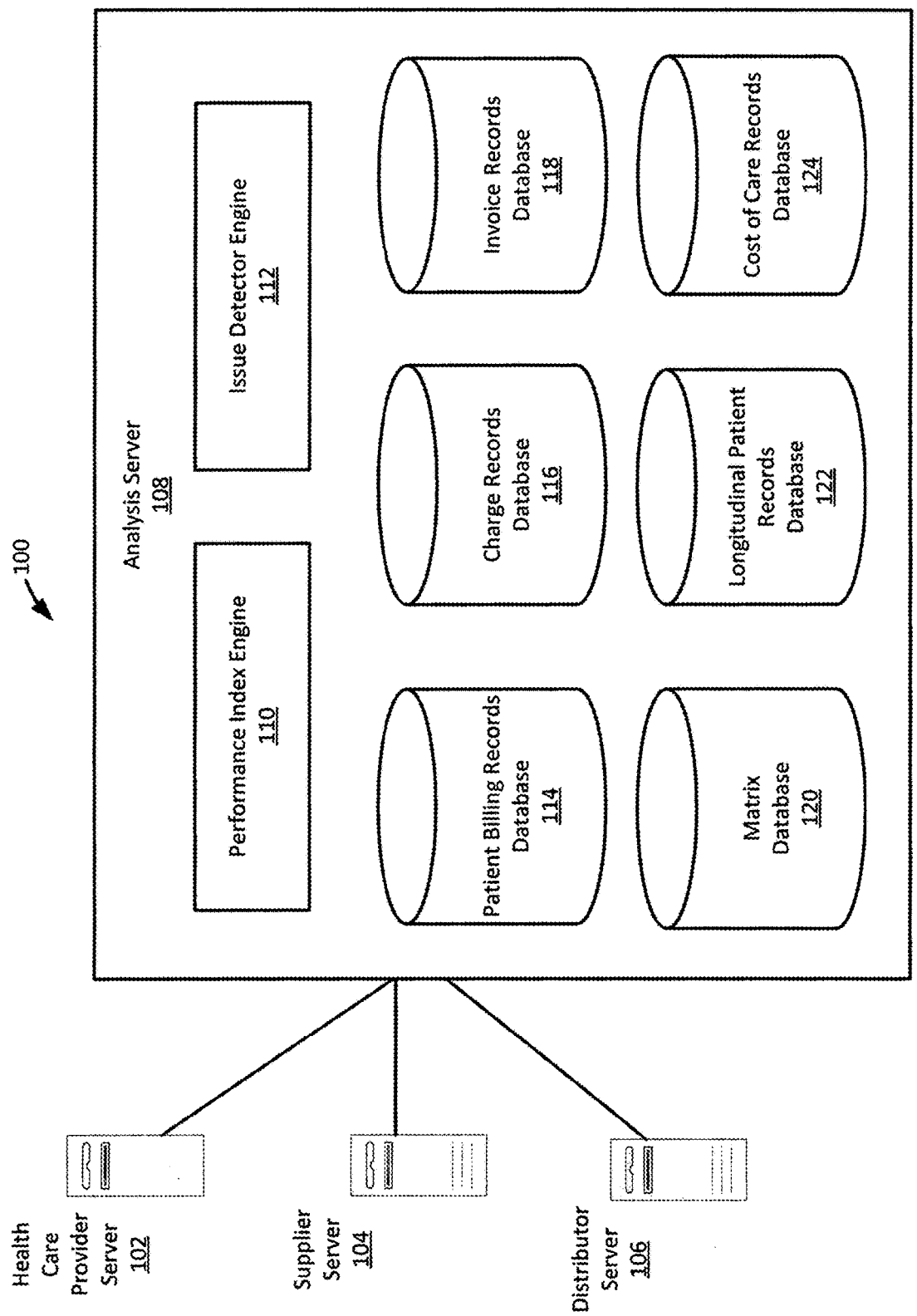
FIG. 1 illustrates a block diagram of a system in accordance with example embodiments.

Persons of ordinary skill in the art will appreciate that elements in the figures are illustrated for simplicity and clarity so not all connections and options have been shown to avoid obscuring the inventive aspects. For example, common but well-understood elements that are useful or necessary in a commercially feasible embodiment are not often depicted in order to facilitate a less obstructed view of these various embodiments of the present disclosure. It will be further appreciated that certain actions and/or steps may be described or depicted in a particular order of occurrence while those skilled in the art will understand that such specificity with respect to sequence is not actually required. It will also be understood that the terms and expressions used herein are to be defined with respect to their corresponding respective areas of inquiry and study except where specific meanings have otherwise been set forth herein.

DETAILED DESCRIPTION

The present invention now will be described more fully with reference to the accompanying drawings, which form a part hereof, and which show, by way of illustration, specific exemplary embodiments by which the invention may be practiced. These illustrations and exemplary embodiments are presented with the understanding that the present disclosure is an exemplification of the principles of one or more inventions and is not intended to limit any one of the inventions to the embodiments illustrated. The invention may be embodied in many different forms and should not be construed as limited to the embodiments set forth herein; rather, these embodiments are provided so that this disclosure will be thorough and complete, and will fully convey the scope of the invention to those skilled in the art. Among other things, the present invention may be embodied as methods, systems, computer readable media, apparatuses, or devices. Accordingly, the present invention may take the form of an entirely hardware embodiment, an entirely software embodiment, or an embodiment combining software and hardware aspects. The following detailed description is, therefore, not to be taken in a limiting sense.

Conventional scoring or benchmarking systems are based upon publicly available sources of data, such as Medicare and Medicaid claims and other Federal and State data reports. Conventional systems do not receive raw data inputs from hospital systems, particularly in the financial (e.g., costs) and clinical encounter areas (e.g., operating room, secondary diagnoses, pharmacy therapies in mixed use delivery settings, etc.). Therefore, conventional systems are missing large swathes of patient data (e.g., commercial plans, self-pay, etc.) and are incapable of isolating or revealing specific, actionable steps that underperforming hospitals could undertake to improve their overall and comparative performance. Existing hospital performance ranking technologies also do not permit hospitals to reveal root causes that are driving important variations in financial, operational and clinical inputs as compared against one or more better performing cohorts. Other conventional ranking systems also do not permit hospitals to directly link other related products or "actionable" solutions that can directly impact or improve each underperforming key performance indicator (KPI).

The example embodiment provide a Performance Index (PI) designed at least to (a) allow hospitals to rank or benchmark itself based upon user-defined financial, operational, clinical and other performance metrics; (b) allow hospitals to define a peer group they will be ranked against using configurable parameters such as type of hospital, geography, bed size, financials, etc.; (c) allow hospitals to "drill into" other hospital's underlying data to determine the root cause of their underperformance as compared to other, anonymized hospitals in the ranking system; and (d) alert hospitals as to specific workflow-driven actions that can be undertaken to alter and improve key performance metrics.

The example embodiments may assist health care entities (e.g., hospitals and other healthcare organizations) with improving their financial and quality performance outcomes utilizing an anonymized comparative hospital database comprised of hospital, related patient records and supply chain/pharmacy cost information imported from a hospital's software applications that manage various departments and functions of the organization (e.g., registration, emergency mom, radiology, billing and claims, laboratory, medical records, charges, pharmacy, etc.). The example embodiments may provide a performance index for comparing a health care provider to its peers, action items for improving performance relative to its peers, recommendations of drugs and/or supplies based on the health care provider's data or peer data on cost of care to improve clinical and financial outcomes, and automated end-to-end ordering of drugs and/or supplies based on the recommended drugs and/or supplies.

FIG. 1 illustrates a block diagram of a system 100 in accordance with example embodiments. System 100 may include a health care provider server 102, a supplier server 104, and a distributor server 106 communicatively coupled to an analysis server 108 by a direct connection or via one or more computer networks (e.g., local area network, wide area network, wireless network, wired network, and the like, and/or some combination thereof).

The health care provider server 102 may send patient data to the analysis server 108 via a patient data feed. A patient data feed may include one or more messages each including data about treatment of a patient. In an example, the analysis server 108 may import patient encounter level data from one or more source hospital systems, and may also import encounter, departmental, service line and other financial data (e.g., charges, etc.) for some or all patient types. The analysis server 108 may also import supply chain, pharmacy cost, purchasing data from a health care provider and/or its supply chain vendor(s). Examples of such data may include hospital purchasing and cost data for pharmacy and medical/surgical supplies at the patient encounter level.

The supplier server 104 may send supply invoice data to the analysis server 108 including information on products and/or services purchased for treatment of one or more patients. The distributor server 106 may send drug invoice data to the analysis server 108. The drug invoice data may include one or more messages including information about drugs purchased by a health care provider and/or its affiliated pharmacy. The analysis server 108 may process the patient data, supply invoice data, and drug invoice data for evaluating health care provider performance.

In an example, the analysis server 108 may include a performance index (PI) engine 110 and an issue detection (ID) engine 112. The PI engine 110 may be configured to generate a performance index for comparing how a health care provider is performing relative to other health care providers (e.g., peers), and the ID engine 112 may detect performance issues and create actions items to enable a health care provider to improve its performance relative to other health care providers. Each of engines 110 and 112, and other components of the analysis server 108 performing the functions described herein, may be discrete pieces of hardware hard coded to perform the functions described herein. In other examples, the functions of engines 110 and 112, and other components, may be implemented in software as computer readable instructions stored in memory whereby execution of the computer readable instructions by at least one processor cause the at least one computer, server, or other device, to perform the functions described herein. In yet other examples, any of the engines and functions described herein may implemented as discrete pieces of hardware and others may be implemented in software. In further examples, some functions performed by an engine may implemented as one or more discrete pieces of hardware and other functions may be implemented in software.

The analysis server 108 may include one or more databases storing information that is processed by the PI engine 110 and the ID engine 112. In an example, the analysis server 108 may include a patient billing records (PBR) database 114, a charge records (CR) database 116, an invoice records (IR) database 118, a matrix database 120, a longitudinal patient records (LPR) database 122, and a cost of care records (CoCR) database 124. The PBR records database 114 may store patient billing records generated from data received from the health care provider server 102 on each encounter with a patient that received a treatment. In an example, the health care provider server 102 may communicate patient data having a patient identifier for identifying a particular patient (e.g., unique alphanumeric sequence, patient's name, etc.), an account identifier for identifying an account of the patient (e.g., an account number), a diagnosis code (e.g., a DRG code), attending practitioner (e.g., doctor, nurse, etc.), area within the health care provider that provided treatment (e.g., outpatient, ER, operating mom, etc.), one or more drug identifiers for identifying what drug(s) was/were administered, one or more supply identifier(s) for indicating what supply(ies) was/were used to treat the patient, and the charges billed to the patient for the treatment. The analysis server 108 may generate a patient billing record that includes the patient data and store the patient record in the PBR database 114.

The CR database 116 may store charge records that associate an account of a patient with one or more charge codes. A charge code may correspond to a supply, drug, or service provided to a patient during treatment. In an example, the health care provider server 102 may provide charge data that may include an account identifier for identifying an account of a patient (e.g., an account number) and one or more charge codes corresponding to charges for treatments provided to the patient. The analysis server 108 may generate a charge record that includes the charge data and store the charge record in the CR database 116.

The IR database 118 may store invoice records that include invoice data on drugs and/or supplies purchased from one or more suppliers and/or distributors. In an example, the supplier server 104 and/or the distributor server 106 may send invoice data that may include a drug or product identifier (e.g., an NDC code for a drug, an alphanumeric sequence for identifying a product, etc.) and its cost. The analysis server 108 may generate an invoice record that includes the invoice data and store the invoice record in the IR database 118.

The matrix database 120 may store mapping rules for mapping proprietary codes of a health care provider to identifiers for products, drugs, or services. In an example, a health care provider may assign a proprietary code to a particular drug that may differ from a national drug code (NDC) for that drug. The rules contained in the matrix database 120 may map the proprietary code to the NDC. Similarly, the mapping rules may map a proprietary code of a health care provider to a standard code of a manufacturer used for identifying a particular supply item.

The longitudinal patient records (LPR) database 122 may include patient-anonymized data aggregated from current (and past) hospital customers through data feeds delivered, for example, securely over a VPN connection on, for example, a real-time or batch daily basis. The data feeds may be encounter-level specific spanning patient, physician, facility, clinical, operational and financial areas.

The analysis server 108 may leverage each of databases 114, 116, 118, 120, and 122 for generating cost of care records that are used to generate comparative performance indices for comparing a health care provider to other, potentially higher performing, health care providers. The cost of care records (CoCR) database 124 may store cost of care records including encounter level data on the costs incurred for treating a patient for a particular ailment. In an example, the analysis server 108 may generate a cost of care record for each patient encounter based on data from one or more of the patient billing records, the charge records, and the invoice records. The analysis server 108 may use the mapping rules to process the patient billing records, the charge records, and the invoice records to determine the cost to treat a patient who has received a particular diagnosis (e.g., assigned a particular diagnosis code). A cost of care record may also include a patient identifier, a diagnosis code, an identifier of the health care provider that provided the treatment, and a cost to treat the patient. The total cost to treat the patient may be a sum of the costs for each drug, supply, and/or labor charge assessed when treating a particular patient for a particular diagnosis code. The cost of care record may also include time and/or date information to indicate when each cost was incurred, location of the treatment (e.g., department within a hospital), practitioner(s) who provided the treatment, length of stay, whether there was an infection, which drug(s) and/or supply(ies) were used to treat the patient.

Below are simple examples of a patient billing record, a charge record, an invoice record, mapping rules, and a cost of care record for a patient diagnosed with osteomyelitis and treated by replacing the patient's hip.

| Patient Billing Record | |
| --- | --- |
| Patient Identifier | Lastname, Firstname |
| Patient Account No. | XRDST1234 |
| DRG Code | 539, osteomyelitis |

| Supply Invoice Record | |
| --- | --- |
| Supplier Name | Acme Medical Corp. |
| Part Name | Acme Hip implant |
| Part No. | ABCDEF |
| Cost | $400 |

| Drug Invoice Record | |
| --- | --- |
| Supplier Name | Allegiant Pharma |
| Drug Name | Morphine |
| NDC | 12345-1234-12 |
| Cost | $100 |

| Charge Record | |
| --- | --- |
| Patient Account No. | 9876543 |
| Charge Code | 12345, Hip implant |
| Charge Code | 56789, Morphine |

| Matrix Rules |
| --- |
| Charge code 12345 = Acme hip Implant ABCDEF |
| Charge code 56789 = Morphine |

| Cost of Care Record | |
|---|---|
| DRG | 539, osteomyelitis |
| Total Cost | $500 (e.g., $400 + $100) |

To create the cost of care record, the analysis server 108 may process the patient billing record to determine an account number of a patient and a DRG code corresponding to the diagnosis for the patient. Here, the DRG code has a value of 539 indicating that a patient was diagnosed with osteomyelitis. The analysis server 108 may use the account number to search the CR database 116 to retrieve a charge record for this treatment. Here, the charge record includes a charge code 12345 for a hip implant and a charge code 56789 for the drug morphine administered during surgery. The analysis server 108 may query the matrix database 120 to map the charge codes to supplier and drug identifiers. Here, charge code 12345 may map to an Acme hip implant having part no. ABCDEF and charge code 56789 may map to morphine having the NDC 12345-1234-12. The analysis server 108 may query the IR database 118 to retrieve invoice records for the Acme hip implant having part no. ABCDEF and for morphine having the NDC 12345-1234-12 to determine the cost of each. Here, the hip implant has a cost of $400 and morphine has a cost of $100. The analysis server 108 may create the cost of care record including the costs to treat this patient diagnosed with osteomyelitis. Here, the cost of care record indicates that the cost to treat this patient having diagnosis code 539, osteomyelitis is $500 (e.g., $400+$100=$500).

The analysis server 108 may generate cost of care records for a particular diagnosis code for analyzing variability in cost to treat patients who have received that diagnosis. In the above example, the diagnosis was osteomyelitis and the analysis server 108 may process the cost of care records to determine, for example, an average cost for a particular hospital to treat patients that receive a hip replacement. The analysis server 108 may also determine a minimum cost, a maximum cost, a cost range, a median cost, or other statistical measure for treating patients assigned a particular diagnosis code. The above-described cost of care analysis may also be performed across every diagnosis code to give a health care provider insight into how much it spends to treat patients who have been assigned each diagnosis code.

Figure 2:
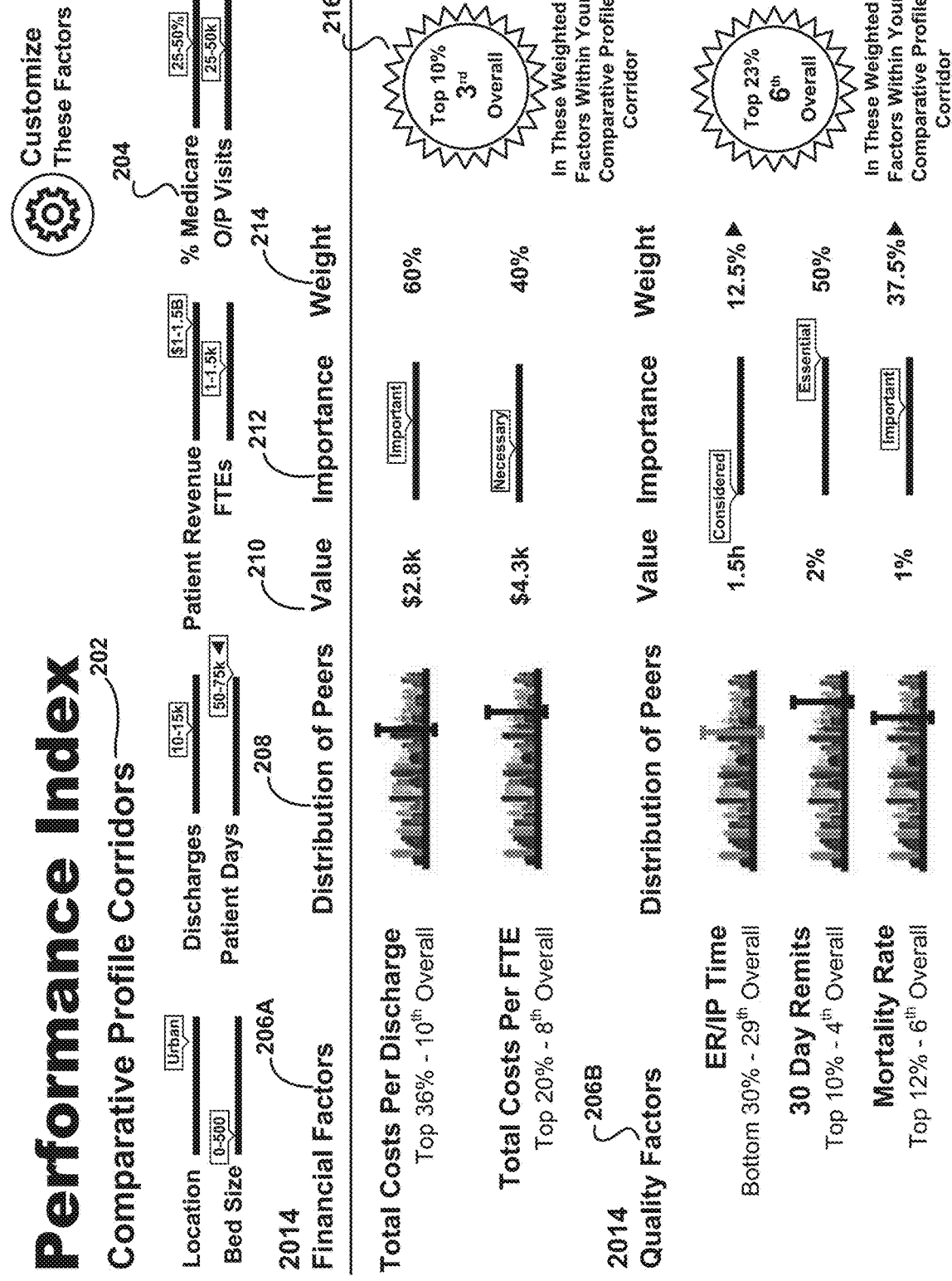
FIG. 2 provides an example graphical user interface (GUI) for presenting a performance index in accordance with example embodiments.

Additionally, the analysis server 108 may aggregate data in the cost of care records for determining variability in a particular health care provider's cost and for comparing its performance to its peers across some or all diagnosis codes. In an example, the performance index (PI) engine 110 may aggregate data from the cost of care records to determine a cost minimum, cost maximum, average cost, standard deviation, and cost range for each health care provider for treatment of patients assigned a particular diagnosis code. The PI engine 110 may utilized the aggregated data to create a performance index to indicate how a health care provider performs relative to other health care providers, and may generate a graphical user interface for presenting the performance index to an interested party, such as for example, an administrator of a health care provider. FIG. 2 provides an example graphical user interface for presenting a performance index in accordance with example embodiments. The performance index graphical user interface (PI GUI) 200 may be a webpage the PI engine 110 serves to a computer or mobile device of a user (e.g., an administrator of a health care provider).

The PI GUI 200 may be configurable permitting a user to select what health care providers are peers of a particular health care provider. In an example, the PI GUI 200 may prompt the user to select inputs for one or more comparative profile corridors 202 to identify what health care providers are considered peers. Examples of comparative corridors may include geographic location of the health care provider, number of beds in the health care provider, number of discharges by the health care provider in a predetermined time frame (e.g., month, year, etc.), number of days patients spend with the health care provider per predetermined time frame (e.g., month, year, etc.), patient revenue per predetermined time frame (e.g., month, year, etc.), full time equivalents (FTEs), percentage of patients on Medicare in a predetermined time frame (e.g., month, year, etc.), number of outpatient visits in a predetermined time frame (e.g., month, year, etc.), and the like. In the depicted example, the comparative profile corridors 202 may be displayed as sliders 204 that a user can adjust to describe its health care provider. For example, a user may manipulate the sliders 204 to indicate that a health care provider is in an urban location, has between 0-500 beds, and has between 25%-50% of its patients on Medicare. The sliders 204 may thus be used to define the set of peer health care providers for comparing a particular health care provider against. The PI GUI 200 may also receive input permitting a user to select between comparing a particular health care provider to its peers for a particular diagnosis code (e.g., DRG for osteomyelitis), for a subset of the diagnosis codes, for a particular area within the health care provider (e.g., ER performance), or for all diagnosis codes. A user may also not provide any input to the corridors 202 for comparison against all health care providers and all diagnosis codes.

In response to the selected corridors, the PI engine 110 may query CoCR database 124 for cost of care records associated with health care providers matching the input comparative profile corridors 202 (e.g., retrieve data on peer health care providers) and optionally matching one or more diagnosis codes and/or areas within the health care provider input by the user. Continuing the above example, the PI engine 110 may retrieve cost of care records for health care providers in urban locations, having between 0-500 beds, and having between 25%-50% of its patients on Medicare. For example, each cost of care record may include metrics on the attributes of the health care provider that contributed data to that record. In another example, the analysis server 108 may store in a health care provider database a table that includes a health care provider record having an identifier for a health care provider and attributes for the health care provider. The analysis server 108 may search the health care provider records based on the input profile corridors 202 for identifying matching health care provider records, and may use the health care provider identifiers from those records for retrieving cost of care records from the CoCR database 124.

The analysis server 108 may use the retrieved cost of care records for comparing a particular health care provider to its peers, as defined by the user via the corridors 202. The analysis server 108 may reveal, through comparative analytics, financial, clinical and operational variations between a health care provider and its peers (E.g., top performing peers), and may recommend specific actionable opportunities that could be taken to improve the health care provider's performance. In an example, the PI engine 110 may process the retrieved cost of care records to generate factors for comparing how the particular health care provider performs in comparison to health care providers in the peer group.

Example factors are financial factors 206A and quality factors 206B. A financial factor 206A may be one or more metrics for comparing how a particular health care provider performs financially relative to health care providers in the peer group. Examples of financial factors may include total cost per discharge, total cost per FTE, etc. A quality factor 206B may be a metric for comparing quality of healthcare provided by a particular health care provider relative to health care providers in the peer group. Examples of quality factors may include emergency room to inpatient time (ER to PP time), readmission rate (e.g., patient readmissions within 30 days), mortality rate, length of hospital stay, reinfection rate, etc. A user may select which financial and/or quality factors to use when generating a performance index, or the PI engine 110 may automatically select which factors to use.

The PI engine 110 may process the retrieved cost of care records to generate at least one statistical measure of the particular health care provider's and its peers' performance for at least one financial factor. In an example, the PI engine 110 may process the retrieved cost of care records to determine a "Total Costs Per Discharge" financial factor for treating patients diagnosed with osteomyelitis. The PI engine 110 may process the cost of care records for the particular health care provider to determine a statistical measures of its cost to treat patients for osteomyelitis (e.g., average total cost), and may determine a similar statistical measure for peer health care providers.

The PI engine 110 may then plot a distribution of peers 208 to illustrate how a particular health care provider performs relative to its peer health care providers for that particular factor. In the depicted example, the x-axis may represent total cost per discharge and the y-axis may identify the number of peer health care providers at each total cost level on the x-axis. The distribution of peers 208 may also include an indicator (e.g., a darkened bar) for signifying where the particular health care provider falls along the distribution. The PI GUI 200 may present additional information to provide context to the user, including in what percentile the particular health care provider falls (e.g., Top 36%), overall rank (e.g., $10^{th}$ overall), and value of the statistical measure 210 (e.g., average of $2,800 total cost per discharge for treating osteomyelitis), for each factor. Similar analysis may be performed to determine other financial factors, as well as the quality factors 206B.

The PI engine 110 may process the factors 206A-B to generating performance indices. In an example, a performance index may be a weighted function of the values of one or more factors. For example, a financial performance index may be a weighted function of the financial factors, a quality performance index may be a weighted function of the quality factors, and a composite performance index may be a weighted function of at least some of the financial performance index and the quality performance index.

Each performance index may be a function of the importance assigned to each factor by the user. In an example, the PI GUI 200 may permit a user to assign an importance weighting to each factor. In the depicted example, the PI GUI 200 may include sliders 204 to specify importance 212 of each factor. Importance 212 may correspond to a point value assigned to a factor in a weighting function. For example, a user may select between importance values of considered, necessary, important, and essential for each factor. Considered may have a point value of 1, necessary may have a point value of 2, important may have a point value of 3, and essential may have a point value of 4. Other point values and names may also be assigned.

The PI engine 110 may total the assigned point values from each importance slider 212 corresponding to the financial factors, the quality factors, or both, to determine a weight 214 assigned to each factor. In the depicted example, the user selected 'important' for the total costs per discharge factor and 'necessary' for the total costs per FTE factor, resulting in a total point value of 5 (e.g., 3+2=5). The PI engine 110 may determine each weighting by dividing a factor's point value by the total point value. In the depicted example, the total costs per discharge factor is assigned a weighting of 60% (e.g., ⅗ *100%=60%) and the total costs per FTE factor is assigned a weighting of 40% (e.g., ⅖ *100%=40%).

The PI engine 110 may then calculate a performance index as a function of the value 210 of each factor multiplied by its weighting. In the depicted example, the PI engine 110 may, for each peer health care provider, multiply the value for total costs per discharge by 60% and multiply the value for total costs per FTE by 40%, and then add the results to determine a weighted result for that health care provider. In the depicted example, the weighted result is $3.4 k (e.g., $2.8 k*0.6+$4.3 k*0.4). The PI engine 110 may then rank the peer health care providers based on the weighted results to determine in what percentile a provider falls relative to its peers, and may update the PI GUI 200 to display a performance metric 216 indicating how the particular health care provider performs relative to its peers. The PI engine 110 may determine that the weighted results of $3.4 k falls in the 92nd percentile, and thus assigns the provider a financial factor performance index of 92. The PI engine 110 may update the PI GUI 200 to display how the healthcare provider performs relative to its peers. In the depicted example, the particular health care provider is in the top 10% and third overall for its financial performance index for the weighted factors within the four selected comparative profile corridors. The PI engine 110 may similarly determine a quality performance index based on the quality factors. A performance index composed of multiple performance indices (e.g., financial and quality performance indices) may be considered a composite performance index (e.g., simple or weighted average of the underlying indices). A user may also select which financial and/or quality factors are used in the weighting function for determining each performance index and a composite performance index.

In additional embodiments, the analysis server 108 may leverage the cost of care records to assist a health care provider in making decisions that improve patient care and improve the health care provider's financial performance. In many instances, there may be a finite number of authorized ways for treating a patient diagnosed with a particular disease or disorder. A particular combination of drug(s) and/or supply(ies) used to treat a patient assigned a particular diagnosis code may be referred to as a treatment modality. In some instances, a treatment modality may be a single drug and/or a single supply item. A health care provider administrator may approve certain drugs and supplies for treating patients having a particular ailment, but may not have sufficient data to support a decision to select a particular combination of drug(s) and/or supply(ies) over other combinations. A health care provider administrator may desire to know which combination leads to a better quality and financial outcome when treating a patient. The analysis server 108 may assist the health care provider in selecting which treatment modality improves patient care and improves the health care provider's financial performance.

Over time, the analysis server 108 may generate the cost of care records indicating how much it costs to treat a particular diagnosis code using different treatment modalities. The PI engine 110 may use the cost of care records to generate performance indices for making recommendations about which treatment modalities to use when treating a patient for a particular ailment. In an example, the PI engine 110 may retrieve some or all of the cost or care records from the CoCR database 124 for patients having the diagnosis code for osteomyelitis. A user and/or the PI engine 110 may limit the cost of care records to a particular health care provider, to peers, a subset of all health care providers, or to all health care providers. Each cost of care record may include the diagnosis code for the ailment at issue (e.g., osteomyelitis) and what treatment modality (e.g., combination of supply(ies) and/or drug(s)) were used to treat the patient. To determine what modality was used, the PI engine 110 may also group the cost of care records that used the same, or substantially the same, supply(ies) and/or drug(s) to treat a patient. For example, 50 patients may have been treated using a first treatment modality where each is given an antibiotic, morphine, and a first type of hip implant, and 75 patients may have been treated using a second treatment modality where each is given morphine, but not antibiotic, and a second hip type of implant. In other examples, the PI engine 110 may identify the treatment modalities based on common use of drug(s) and/or supply(ies), a cost of care record may specify what treatment modality was used, or a user may specify what drug(s) and/or supply(ies) constitute each modality.

The PI engine 110 may process the cost of care records for determining one of more factors (e.g., financial factors, quality factors) for each treatment modality. The PI engine 110 may then aggregate the data from each cost of care record by modality, and generate a performance index for each modality as a weighted function of the one or more factors. In an example, the PI engine 110 may determine for the first modality that total costs per discharge financial factor may have an average cost of $2.2 k and the total costs per PTE may have an average cost of $3.8 k. The PI engine 110 may determine for the second modality that total costs per discharge financial factor may have an average cost of $2.6 k and the total costs per PTE may have an average cost of $3.9 k. If the total costs per discharge financial factor is ranked 'important' and the total costs per FTE is ranked 'necessary', then the PI engine 110 may determine a weighted value of $2.84 k (e.g., $2.2 k*0.6+$3.8 k*0.4=$2.84 k) for the first modality and $3.12 k for the second modality (e.g., $2.6 k*0.6+$3.9 k*0.4=$3.12 k). The PI engine 110 may determine a performance index for each modality based on the percentage of peer weighted values that fall below each weighted value. For example, the PI engine 110 may determine that the first treatment modality has a financial factor performance index score of 85 as it is in the 85% percentile and that the second treatment modality has a financial factor performance index score of 77 as it is in the 77% percentile. The PI engine 110 may rank the performance indices to rank the treatment modalities relative to one another. The PI engine 110 may determine healthcare factor performance indices in a similar manner and determine a composite performance index for each treatment modality. For example, the PI engine 110 may average a financial factor performance index and a healthcare factor performance index to determine a composite performance index for each modality. In another example, the PI engine 110 may assign weights to the financial factor performance index and a healthcare factor performance index and may determine the composite performance index for each modality as a weighted average of the indices (e.g., composite performance index=[financial factor performance index*weight w1+healthcare factor performance index*weight w2]/2). It is noted that a composite performance index may be a function of other performance indices, instead of or in addition to financial and quality performance indices. The PI engine 110 or a user may select the underlying performance indices to be used in a composite performance index.

The PI engine 110 may then select one of the treatment modalities based on the ranked performance indices. For example, the PI engine 110 may select the treatment modality having a highest performance index, signifying a lowest cost and best quality outcome for patients. The PI engine 110 may thus recommend which modality to use when subsequently treating patients for that particular ailment. The modality recommendation may provide a holistic view of treatment costs, and thus may provide recommendations of when it makes sense to use a more expensive drug and/or supply, and when it does not. It is noted that recommendations may change over time as new drugs and/or supplies become available. Further, the definition of peer health care providers, which may use different drugs and/or supplies than a particular health care provider, may also impact a recommended modality.

A recommended treatment modality may also be demographic-based. For example, the analysis server 108 may process the cost of care records to determine that the second treatment modality may provide better performance when used for a particular demographic group (e.g., Caucasian women aged 60-65), and the first treatment modality may provide better performance for other demographic groups. This demographic-based recommendation may be provided to a practitioner when scheduling treatment (e.g., a hip replacement).

The analysis server 108 may also control ordering of inventory of drugs and/or supplies based on a recommended treatment modality. In an example, the analysis server 108 may determine that a particular treatment modality provides a better outcome for patients and the health care provider, and when time to order supplies and/or drugs, the analysis server 108 may communicate an order message to the supplier server 104 and/or the distributor server 106 to order the supplies and/or drugs for the recommended modality. For example, the analysis server 108 may automatically order the supplies and drugs for the first treatment modality, and not the second, from the supplier server 104 and the distributor server 106. In other examples, the analysis server 108 may prompt for administrator approval to order the particular drugs and/or supplies, instead of automatically ordering. The quantity ordered may be based on an estimated number of supplies and/or drugs needed (e.g., estimated number of hip implants) to be performed in a predetermined amount of time. For example, a health care provider may average performing 15 hip implants per month, and thus an appropriate quantity of morphine and the first hip implant may be ordered to meet anticipated demand. The supplier server 104 and the distributor server 106 may receive the respective order messages, and may have a person or a robotic system fulfill the respective orders and cause shipment of the ordered supply(ies) and/or drug(s) to the health care provider.

In some examples, the analysis server 108 may assign an urgency level for each order. Example urgency levels may include routine, expedited, and next day. Devices of workers at a supplier warehouse and/or at a distributor warehouse may include shipment software applications. Example worker devices include tablet computers, smart phones, computers, and the like. In response to receiving an order message, the shipment software application may activate a worker device to display a GUI with the order and its urgency level. In some instances, receipt of an alert message having a higher urgency level may cause the shipment software application to establish a network connection to analysis server 108 to receive any additional data on an order. The ID engine 112 may also coordinate with the shipment software application of the device to route the order message to multiple devices associated with different workers that may fulfill the order, particularly if an order has a higher urgency level.

The order may also be based on demographics of patients served by the health care provider. In some instances, the health care provider may desire to have a certain inventory level on site and may order drugs and/or suppliers in anticipation of demand. If the recommendation determines that some drugs and/or products are more effective for a particular demographic group, the analysis server 108 may order those drugs and/or products in proportion to the members of the particular demographic group that are served by the health care provider. For example, the analysis server 108 may determine that it averages replacing 100 hips per month, with 15% of those hip replacements being for Caucasian women aged 60-65. The recommendation may be the second treatment modality for Caucasian women aged 60-65 and the first treatment modality for everyone else. The analysis server 108 may thus order 85 of a hip specified in a first modality and 15 of a hip specified in a second modality.

The system 100 may thus provide a fully automated end-to-end solution for data driven recommendations of which drugs and/or supplies to order. A person may only provide oversight, whereas the system 100 may determine what supplies and/or drugs lead to better patient and financial outcomes, and automatically order those supplies and/or drugs for delivery to the health care provider.

The analysis server 108 may also assist a user (e.g., health care provider administrator) in adjusting health care provider procedures and ordering of supplies and/or drugs to improve its performance index. To do so, the analysis server 108 may include an issue detector (ID) engine 112 to identifying action items for identifying issues that a health care provider may use to improve its financial and/or quality factors. In an example, the ID engine 112 may process cost of care records for a particular health care provider for identifying supply chain issues, pharmacy issues, and/or revenue integrity issues that impact the health care provider's performance relative to its peers.

Figure 3:
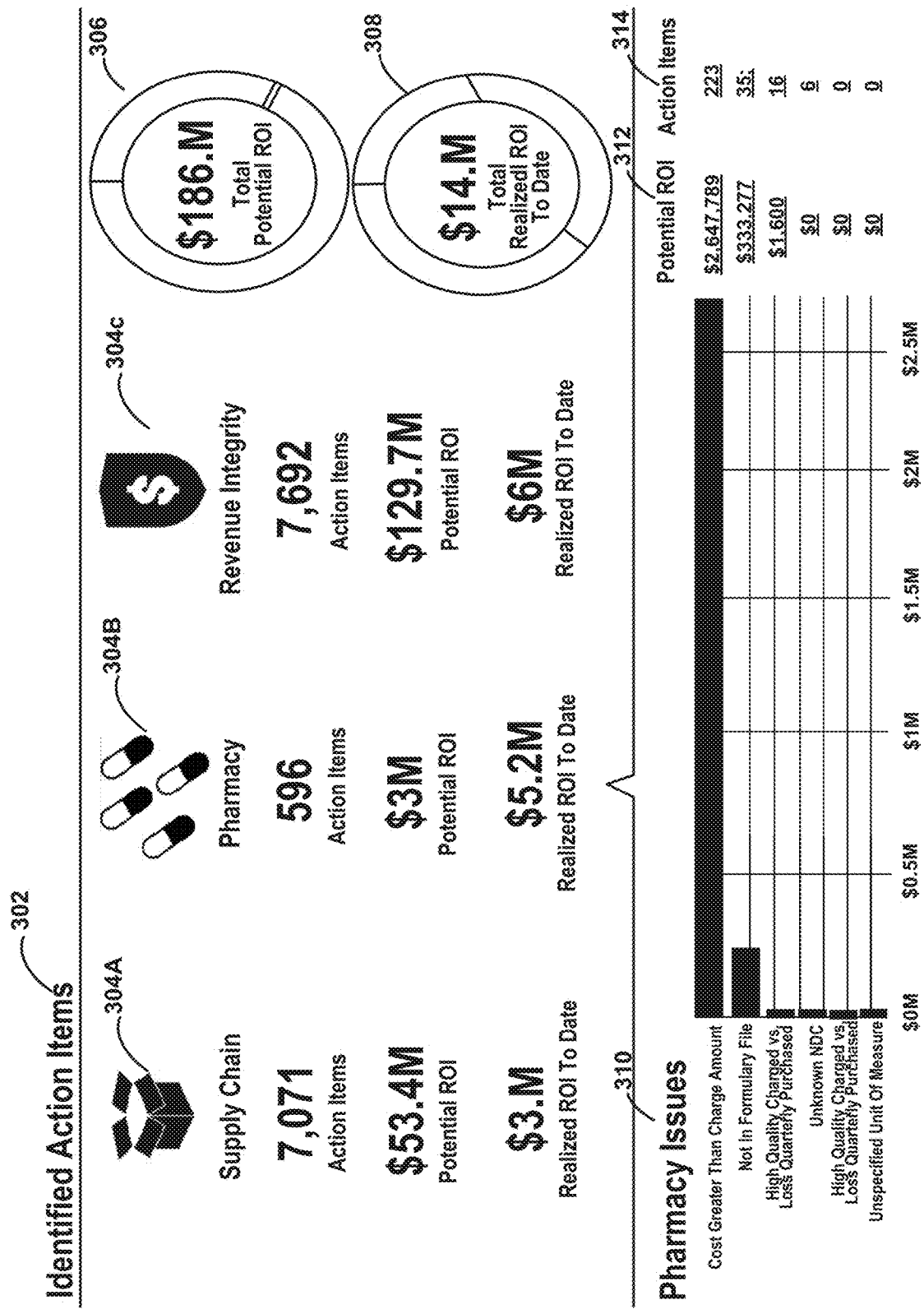
FIG. 3 illustrates an example Action Item (AI) GUI in accordance with example embodiments.

In an example, the ID engine 112 may generate an Action Item (AI) GUI to display action items that a health care provider may undertake to improve its performance index. FIG. 3 illustrates an example AI GUI in accordance with example embodiments. The AI GUI 302 may list supply chain action items 304A, pharmacy action items 304B, and revenue integrity action items 304C. For each action item 304, the AI GUI 302 may list a total number of action items, a potential amount of return on investment, and an amount of return on investment a health care provider has realized by correcting actions items. In the depicted example, the supply chain action item 304A may indicate that there are a total of 7,071 supply chain action items representing $53.4 million in potential return on investment (ROI), and that the health care provider has realized $3 million return on investment to date by correcting previously identified action items. The AI GUI 302 may also identify a total potential ROI 306 and a total realized ROI to date 308. In the depicted example, the total potential ROI is $186 million and the total realized ROI to date is $14 million.

The Action items 304 may be selectable by a user for displaying additional information about the selected action item. In the depicted example, a user may select the pharmacy action items 304B and the ID engine 112 may update the AI GUI 302 to display one or more classes of pharmacy issues, a potential ROI 312 for each issue class, in aggregate, for each class of pharmacy issue, and a total number of action items 314 falling within each issue class. To generate the AI GUI 302, the ID engine 112 may apply issue detection logic to process the cost of care records, patient billing records, charge records, and invoice records searching for issues. The following describes algorithms for searching for pharmacy issues, supply chain issues, and revenue integrity issues.

Below are a number of example pharmacy issues the ID engine 112 may detect.

In a first example, the ID engine 112 may tie drug purchasing to drug utilization by identifying drugs that were purchased in a quantity that is less than the number of times a patient was charged for that drug. The ID engine 112 may identify drugs, by NDC, in which the total number of patient charges for a drug is in excess of the quantity of the drug purchased by the health care provider. In an example, the ID engine 112 may search the invoice records and the charge records looking for a discrepancy where patients have been charged for a larger quantity of a drug than the health care provider purchased. The ID engine 112 may create an action item for each identified discrepancy.

In a second example, the ID engine 112 may tie drug purchasing to drug utilization in another manner by identifying drugs that were purchased in a quantity that exceeds the number of times patients were charged for that drug. The ID engine 112 may identify drugs, by NDC, in which the quantity of a drug purchased by the health care provider exceeds the dispensed quantity of the drug charged to patients. In an example, the ID engine 112 may search the invoice records and the charge records looking for a discrepancy where a larger quantity of a drug was purchased than a dispensed quantity of the drug charged to patients. In this determination, the ID engine 112 may account for product that remains in inventory that has not yet been dispensed. The ID engine 112 may create an action item for each identified discrepancy.

In a third example, the ID engine 112 may identify any drugs that were purchased but are not in a formulary file. A formulary file may be a listing of drugs that are available to be dispensed by the health care provider. The ID engine 112 may identify drugs, by NDC, that the health care provider purchased but are not on the health care provider's formulary file. In an example, the ID engine 112 may search the invoice records to identify some or all drugs a health care provider has purchased, and compare the identified drugs to the health care provider's formulary file for identifying any discrepancies. The ID engine 112 may create an action item for each identified discrepancy.

In a fourth example, the ID engine 112 may identify any drugs that cost more than the amount a patient was charged for the drug. The ID engine 112 may compare the amount a patient is charged, as listed in a charge record, with the amount a drug cost as listed in an invoice record. For example, the ID engine 112 may determine where a single charge unit acquisition cost for a drug is greater than a corresponding charge amount, accounting for the quantity dispensed and the purchase price attributable to that quantity. The ID engine 112 may create an action item for each identified instance.

In a fifth example, the ID engine 112 may identify any drugs having an unknown NDC code. To do so, the ID engine 112 may compare a particular NDC retrieved from an invoice record with a list of known NDC codes to determine if the particular NDC is on the list. If not on the list, the ID engine 112 may create an action item indicating that the drug has an unknown NDC code.

In an sixth example, the ID engine 112 may identify any drugs in a formulary file having an unspecified unit of measure. For example, a formulary file may list "null" as the value for either package size or package quantity of a drug. If a drug does not have a specified unit of measure, the health care provider cannot track how much of the drug has been dispensed nor determine whether the health care provider is charging a patient at least the cost the health care provider paid for a particular quantity of the drug (e.g., charge a patient at least $1.50 per pill for a drug the health care provider purchased for $1.50 per pill). The ID engine 112 may create an action item for each identified instance.

Subsequent to identifying the issues, the ID engine 112 may categorize the issues into classes and update the AI GUI 302 to display the identified issues. For example, the ID engine 112 may use the identified issues for populating a pharmacy issues table 310. The ID engine 112 may also determine a potential ROI 312 for each issue class and a total number of action items 314 per issue class. In the depicted example, the AI GUI 302 may display the following pharmacy issue classes: Cost greater than charge amount, Not in formulary file, High quantity charged vs. low quantity purchased, Unknown NDC, High quantity charged vs. low quantity charged, and Unspecified unit of measure. Other issue classes may be identified in addition to or instead of these issue classes. In the depicted example, the Cost greater than charge amount issue class may have 223 action items with an aggregate potential ROI of $2,647,789.

The analysis server 108 may also assist a user in resolving the identified action items. With reference to FIG. 3, a user may select a particular one of the pharmacy issue classes of the AI GUI 302. For example, a user may select the Cost Greater Than Charge Amount pharmacy issue class in AI GUI 302. In response, the ID engine 112 may present an issue class GUI 400, an example of which is shown in FIG. 4 depicting the Cost Greater Than Charge Amount pharmacy issue class 402. The issue class GUI 400 may identify each drug where the health care provider is charging a patient less than what a drug costs. In an example, the issue class GUI 400 may include a table where each row lists a drug by NDC 404, charge code 406, dispensation cost 408, charge amount 410, and financial impact 412. The dispensation cost 408 may be the cost a health care provider incurred to by a drug and the charge amount 410 may be the amount the health care provider charged a patient for the drug. The dispensation cost 408 and the charge amount 410 may also be averages. In the depicted example, the dispensation cost 408 is $573.60 and the charge amount 410 is $102, meaning that the health care provider is losing $471.60 each time it dispenses that drug to a patient. The financial impact 412 may be a running total indicating how much the health care provider has lost by charging its patients less than the cost to purchase the drug. The pharmacy issue GUI 400 may include a resolve field 414 prompting the user to resolve the cost discrepancy. In response to selection of the resolve field 414, the ID engine 112 may present a resolution GUI, an example of which is shown in FIG. 5.

The resolution GUI 500 may display information about a drug that costs more than what a health care provider is charging its patients for the drug, and may prompt the user to selection from one or more resolution options 502. Example resolution options may include prompting the user to purchase a generic that is equivalent to the drug, change the amount charged to patients, and ignore the action item. In the depicted example, the resolution GUI 500 prompts the user to choose between selecting an alternative drug (e.g., a cheaper generic or branded drug) 504A, updating a charge amount 504B, and ignoring the action item 504C.

In an example, the ID engine 112 may generate a list of alternatives drugs by identifying any drug that is an equivalent medication. The ID engine 112 may recommend and/or automatically select an alternative drug. For example, the ID engine 112 may access a drug database listing drugs having equivalent active ingredients and a cost of each drug. The ID engine 112 may select a drug having a lowest cost that has the same or equivalent active ingredient. The ID engine 112 may recommend the cheapest, equivalent drug to the user (e.g., health care provider administrator) for approval. In another example, the ID engine 112 may automatically order the cheapest, equivalent drug, instead of the more expensive drug, from a drug distributor. For example, the analysis server 108 may determine current inventory levels for the more expensive drug. When inventory falls below a predetermined level, the analysis server 108 may, for example, communicate an order message to the drug distributor server 106 ordering the cheapest, equivalent drug, instead of the more expensive drug. The drug distributor server 106 may receive the order message, and may have a person or a robotic system fulfill the order and cause shipment of the cheapest, equivalent drug to the health care provider. The analysis server 108 may also inform practitioners about the less expensive alternative.

The resolution GUI 500 may also permit a user to update the amount a patient is charged for a drug. When the dispensation cost exceeds the charge amount, a user may input an updated charge amount into the resolution GUI 500. In another example, the ID engine 112 may automatically update a charge amount in response to detecting that a dispensation cost exceeds a charge amount. To do so, the ID engine 112 may include a formula for adjusting the dispensation cost such that it is less than a charge amount. In an example, the ID engine 112 may determine an average dispensation cost, and adjust the charge amount such that it is greater than the average by at least a predetermined amount. The predetermined amount may be a fixed amount and/or a percentage above the dispensation cost. For example, a health care provider may specify that the charge amount provides at least a 5% profit margin on all drugs. The ID engine 112 may update a charge amount to be the average dispensation cost multiplied by 1.05. Using the example depicted in FIG. 5, the ID engine 112 may automatically update the charge amount to be $602.28 (e.g., $573.60*1.05) associated with a charge code for that drug in an accounting system of the health care provider. In another example, the ID engine 112 may update the charge amount to exceed the dispensation cost by a fixed amount (e.g., $5). The automatic updating of charge amounts may occur in real time and thus result in real-time changes in the health care provider's dispensation costs. A health care provider may thus realize significant savings by utilizing the ID engine 112 to make sure the health care provider is not charging patients less than the cost the health care provider paid for a drug. Conventional systems, for comparison, may not identify such a loss resulting in a significant detrimental financial impact that can last for 30 days or worse.

In some examples, the ID engine 112 may assign an urgency level for each action item. Example urgency levels may include routine, urgent, and extremely urgent. In an example, the ID engine 112 may assign the urgency level based on potential ROI determined for an action item. For example, the ID engine 112 may assign a routine urgency level for action items having a potential ROI less than a first threshold, an urgent urgency level for action items above the first threshold and up to a second threshold, and an extremely urgent urgency level for action items above the second threshold. The ID engine 112 may determine whether to communicate an alert to a user (e.g., healthcare provider administrator) based on the urgency level. For example, an Action Item software application may run on a user device (e.g., laptop, mobile phone, smartphone, etc.). Assigning an action item an extremely urgent urgency level may trigger the ID engine 112 to communicate an alert message to the user device for activating the Action Item software application. In response to receiving the alert message, the Action Item software application may cause the user device to display the action item assigned an extremely urgent urgency level in the AI GUI 302. Receipt of the alert message may cause the Action Item software application to establish a network connection to the ID engine 112 to receive any additional data on action item at issue. The ID engine 112 may also coordinate with the Action Item software application of the user device to route the alert message to multiple user devices associated with the user (e.g., forward alert message to a user's smartphone, tablet computer, and desktop computer). The alert message may also instruct the Action Item software application to cause the user device to emit a sound corresponding to the urgency level.

Figure 6:
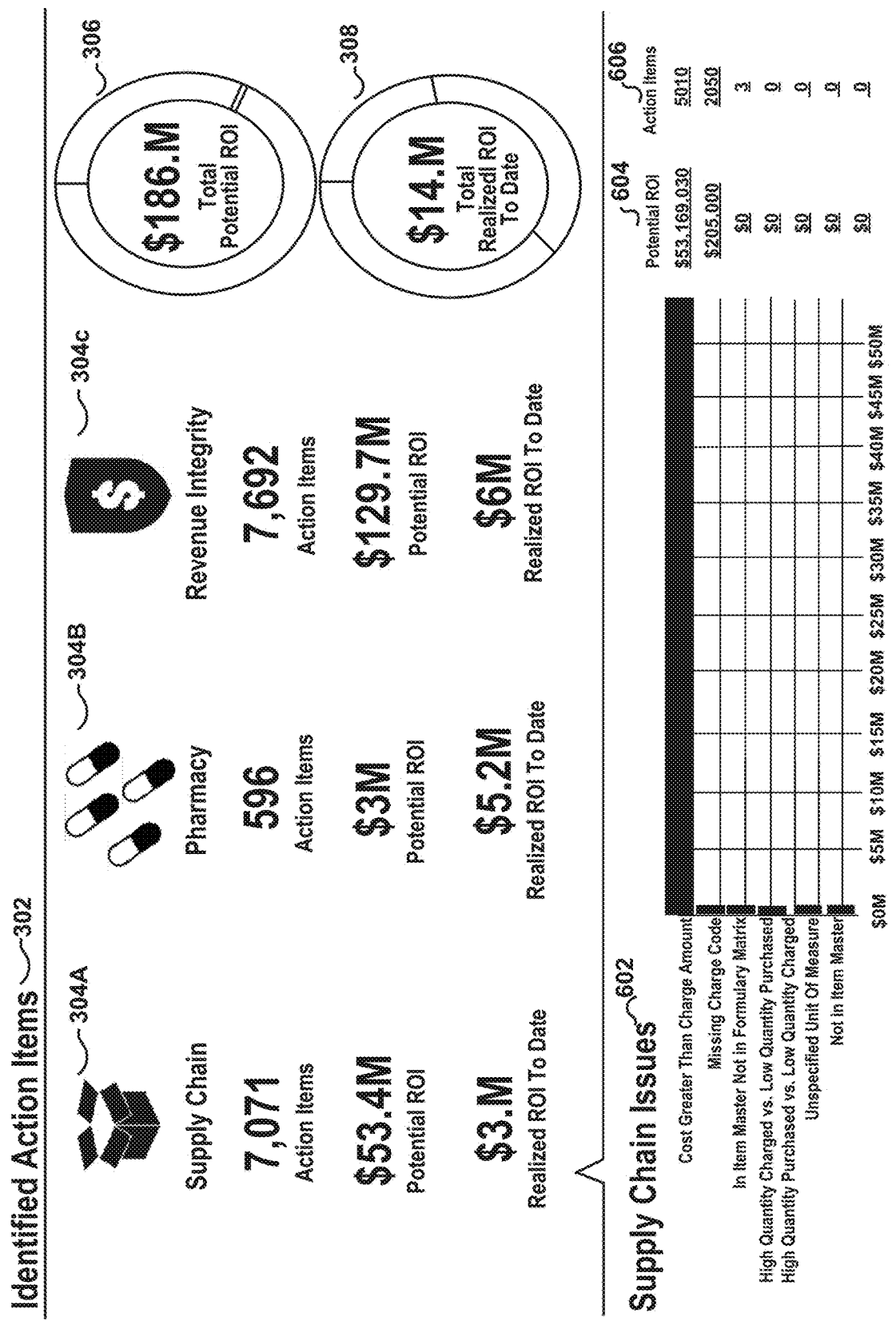
FIG. 6 illustrates an example of the AI GUI depicting classes of supply chain issues in accordance with example embodiments.

In addition to pharmacy issues, the analysis server 108 may identify supply chain issues. FIG. 6 illustrates an example of the AI GUI 302 depicting classes of supply chain issues. Similar to the description above, a user may select the supply chain action item 304A and the ID engine 112 may update the AI GUI 302 to display a table listing classes of supply chain issues 602. As in the description of pharmacy issues, the AI GUI 302 may display classes of supply chain issues, a potential ROI 604 for each class, and a total number of action items within each class 606.

Below are a number of examples of supply chain issues the ID engine 112 may detect. In a first example, the ID engine 112 may tie supply purchasing to utilization by identifying supply items that were purchased in a greater quantity than the amount patients were charged for those supply items. The ID engine 112 may also determine a common unit of measure to equate purchases with charges where an item is purchased in a larger quantity than what is used to treat a patient (e.g., buy 1,000 cotton swaps and only average using 3-5 per patient). To do so, the ID engine 112 may identify supplies in which the quantity of the item patients were charged is less than the quantity of the item purchased by the health care provider. In an example, the ID engine 112 may search the invoice records and the charge records looking for a discrepancy where patients have been charged for fewer items than purchased by the health care provider. The ID engine 112 may also account for damaged supplies and search for instances where the quantity of an item purchased exceeds the quantity charged to patients, accounting for any unused quantity remaining in inventory. The ID engine 112 may create an action item for each identified instance.

In a second example, the ID engine 112 may tie supply purchasing to utilization by identifying supplies where the health care provider purchased a smaller quantity of an item than the number of times patients were charged for that item. The ID engine 112 may also determine a common unit, as described above. To do so, the ID engine 112 may identify supplies in which the total number of patient charges for a particular item exceeds the quantity of the item purchased by the health care provider. In an example, the ID engine 112 may search the invoice records and the charge records looking for a discrepancy where patients have been charged for a greater number of items than purchased by the health care provider. The ID engine 112 may also account for damaged supplies and search for instances where the quantity of an item purchased exceeds the quantity charged to patients, accounting for any unused quantity remaining in inventory. The ID engine 112 may create an action item for each identified instance.

In a third example, the ID engine 112 may identify any supplies having a purchase cost that exceeds the amount charged to a patient. To do so, the ID engine 112 may search a charge data master identifying how much a patient is being charged for a particular item. The ID engine 112 may search the invoice records to identify some or all supplies a health care provider has purchased, and compare the identified supplies to the health care provider's charge data master for identifying instances where a patient is charged less than an item costs to purchase. The ID engine 112 may create an action item for each identified instance.

In a fourth example, the ID engine 112 may identify any supplies that are in an item master file, but not in a supply formulary file. The item master file may list all of the supplies a health care provider can provide to a patient, and the supply formulary file may be list mappings of proprietary codes the health care provider assigns to an item with a generic identifier of the supply item. The ID engine 112 may compare the item master file to the supply formulary file to identify items that are present in the Item Master, but not in the supply formulary file. The ID engine 112 may create an action item for each identified instance.

In a fifth example, the ID engine 112 may identify any supply items that are being purchased but are not associated with an item in the item master file. To do so, the ID engine 112 may search the invoice records to identify what items are being purchased, and may then attempt to match each purchased item with a supply item listed in the item master file. The ID engine 112 may then list all of the items not having a match and may create an action item for each identified instance.

In an sixth example, the ID engine 112 may identify any supply items that do not have a charge code. To do so, the ID engine 112 may look for any instances provided in the item master file that do not have an assigned charge code. The ID engine 112 may create an action item for each identified instance. In some examples, if any such instances are found, the ID engine 112 may automatically update the item master file to include a charge code and a charge amount. The updated charge amount may be based on the cost of a unit of the supply item, plus a fixed amount or a predetermined profit margin.

The ID engine 112 may use the identified issues for populating the supply issues table 602 that includes information on classes of supply chain issues, potential ROI 604, and action items 606.

Figure 7:
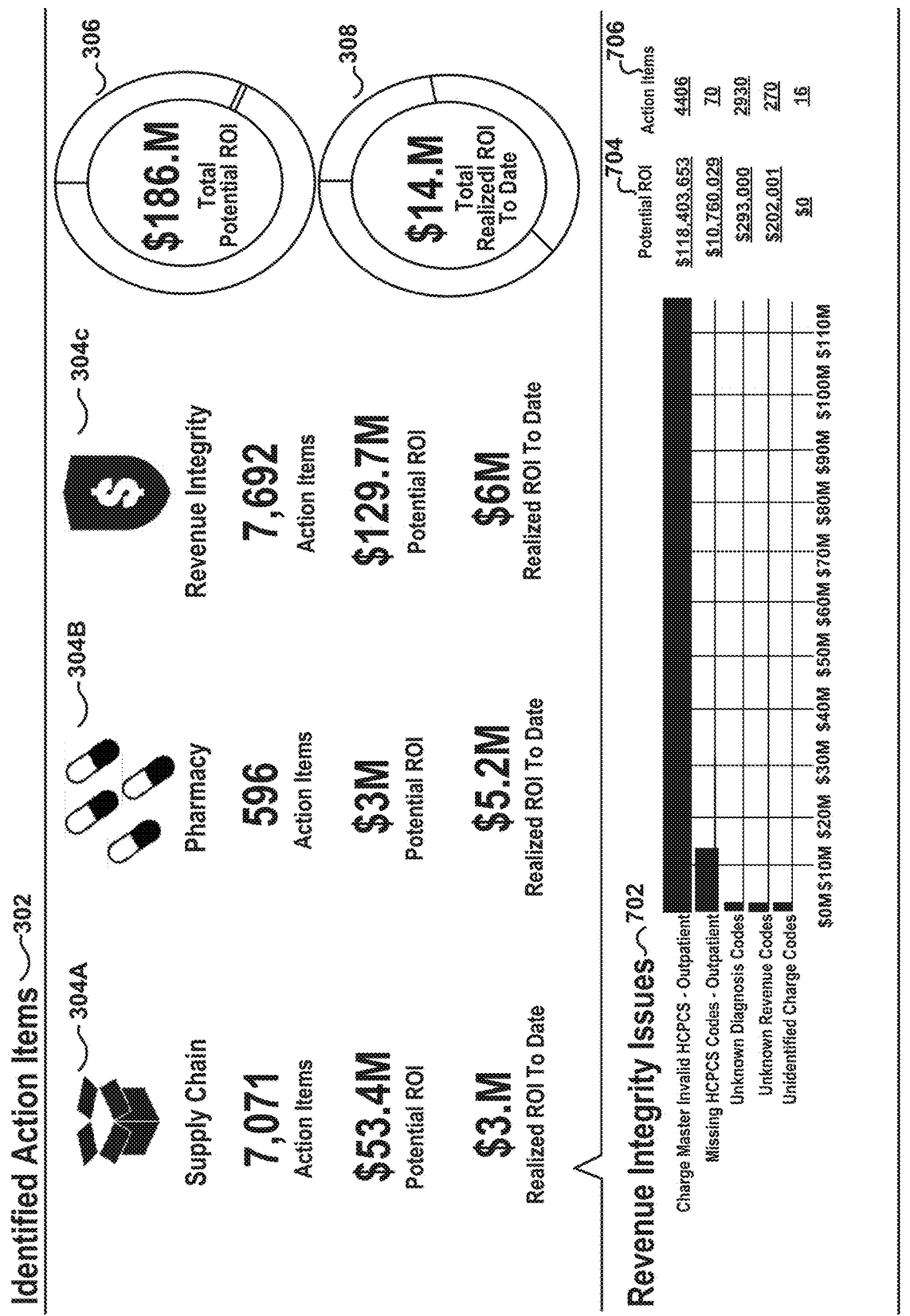
FIG. 7 illustrates an example of the AI GUI depicting classes of revenue integrity issues in accordance with example embodiments.

In addition to detecting supply chain and pharmacy issues, the analysis server 108 may identify revenue integrity issues. FIG. 7 illustrates an example of the AI GUI 302 depicting classes of revenue integrity issues. Similar to the description above, a user may select the revenue integrity action item 304C and the ID engine 112 may update the AI GUI 302 to display classes of revenue integrity issues 702. As in the description of supply chain and pharmacy issues, the AI GUI 302 may display classes of revenue integrity issues, a potential ROI 704 for each class, and a total number of action items within each class 706.

Below are a number of examples of revenue integrity issues the ID engine 112 may detect. In a first example, the ID engine 112 may analyze diagnosis codes assigned to each patient encounter for identifying instances where the diagnosis is invalid. The ID engine 112 may compare an assigned diagnosis code in each LPA to a list of valid diagnosis codes to identify any assigned codes that are not on the list. The ID engine 112 may create an action item for each invalid diagnosis code.

In a second example, the ID engine 112 may analyze a charge data master to identify charge records having an invalid healthcare common procedure coding system (HCPCS) code. The ID engine 112 may compare an assigned HCPCS code in each longitudinal patient record to a list of valid HCPCS codes to identify any assigned HCPCS codes that are not on the list. The ID engine 112 may create an action item for each invalid HCPCS code.

In a third example, the ID engine 112 may identify any charge codes that are not in a charge data master. To do so, the ID engine 112 may analyze the charge records to identify charge codes that have been used and may compare the identified charge codes to find instances where a charge code is not present in a charge data master. The ID engine 112 may create an action item and may add the charge code to the charge data master.

In a fourth example, the ID engine 112 may identify any unknown charge codes. To do so, the ID engine 112 may analyze the identified charge codes in the charge records and compare the identified charge codes to find instances where a charge code is not present in a list of valid charge codes. The ID engine 112 may create an action item for each unknown charge code.

In a fifth example, the ID engine 112 may identify charges where a health care provider is missing out on a reimbursement opportunity, such as for outpatients. To do so, the ID engine 112 may analyze the identify charge codes in the charge records used in an outpatient setting and compare the identified charge codes to identify charge codes that have no HCPCS code in the Charge Data Master. The ID engine 112 may create an action item for each reimbursement opportunity.

The ID engine 112 may use the identified issues for populating the revenue integrity table 702.

The analysis server 108 may also rank the actions items for providing a user (e.g., a health care provider administrator) recommendations on which action items to address first to yield a greatest improvement in the health care provider's performance index. The recommendations may be suggested changes to a health care provider's financial, clinical and/or operational workflow, processes, and decisions. For example, the ID engine 112 may rank each of the action items based on potential ROI. In some instances, the ID engine 112 may automatically address the action item. For example, if a health care provider is charging patients less than the cost of a drug, the ID engine 112 may automatically update a charge amount associated with a charge code to at least be the same as or greater than the cost of the drug (e.g., at least a 5% profit margin). The ID engine 112 may also predict an improvement for a performance index based on fixing one or more action items. For example, the engine 112 may predict that a health care provider will more from the top 25% to the top 20% if it addresses three particular action items having the top three highest potential ROIs.

Further, the ID engine 112 may generate a number of reports on performance of the health care provider's pharmacy, supply chain, and revenue integrity. In an first example, the ID engine 112 may generate a Pharmacy Cost Variance by Charge Code report. To generate this report, the ID engine 112 may process charge records and drug invoice records using the mapping rules on a charge code by charge code basis for each drug that has been dispensed to a patient. For example, the ID engine 112 may search the charge records database 116 for charge records having charge code 56789 for the drug morphine, utilize mapping rules from the matrix database 120 to map the morphine charge code to its NDC (e.g., 12345-1234-12), and search the invoice records database 118 for invoice records having morphine's NDC. The ID engine 112 may then perform statistical measures to determine, for example, the minimum, maximum, and average purchase prices the health care provider paid for morphine, standard deviation, total purchase volume, and the number of outlier purchases. In some instances, multiple drugs may be mapped to a single charge code, and thus the statistical analysis may apply for some or all drugs mapped to that charge code. While the above example referenced morphine, the ID engine 112 may perform a similar analysis for some or all drugs in the health care provider's formulary file. Moreover, the ID engine 112 may perform a similar analysis for determining supply cost variance by charge code.

In a second example, the ID engine 112 may generate a readmissions report. The ID engine 112 may retrieve longitudinal patient records from the LPR database 122. Each longitudinal patient record may include data on a patient's zip code, number of readmissions, a count of the number of encounters, and a readmission ratio percentage. To generate the readmissions report, the ID engine 112 may determine an aggregate breakdown by Zip Code of the number of readmissions, the count of encounters, and the readmission ratio percentage over a predetermined for a predetermined amount of time (e.g., prior month, quarter, year, etc.) for inclusion in the readmissions report. The readmissions report may include a drill down feature providing patient name, primary diagnosis code, primary diagnosis description, and the number of readmissions. The readmissions report may also provide a link for those patients included in the report period and permit the user to access the LPR database 122 for more details on that specific patient.

In a third example, the ID engine 112 may generate a Two Midnight Rule report. A Two Midnight Rule report may provide a list of patients who were billed as an inpatient but did not stay for two midnights (e.g., used to pass a Medicare review). To generate the Two Midnight Rule report, the ID engine 112 may access the longitudinal patient records to identify how many, if any, patients who were billed as an inpatient but did not stay for two midnights.

In a fourth example, the ID engine 112 may generate an episodes of care (EOC) report. An EOC report may provide a breakdown by Patient Status for both inpatient and outpatient, along with their respective number of patient encounters, average charge amounts, and the average length of stay. The information displayed may be for a predetermined time period (e.g., for a rolling 12-month period). The EOC report may provide a drill down feature for those patients included in the report period and may ling to the LPR database 122 for more details on specific patients.

In a fifth example, the ID engine 112 may generate a Total Cost of Care (TCOC) report. The TCOC report may provide an aggregate breakdown by various age groups of patient encounters, charge amounts, and acquisition costs. The information displayed may be for a predetermined time period (e.g., for a rolling 12-month period).

In a sixth example, the ID engine 112 may provide Patient Encounter Cost Variance (PECV) report. The PECV report may provide variances of patient encounter costs by primary diagnosis for a predetermined time period (e.g., a rolling 12-month period). The PECV report may display details on one or more of: Code, (code) Description, Minimum Encounter Cost, Maximum Encounter Cost, Median Encounter Cost, and Encounter Cost Range.

The analysis server 108 may also review the health care provider's contracts relative to the invoice records to determine how the health care provider can better leverage its existing contracts. In many instances, a health care provider may enter into a contract with a drug company, a supplier, or other entity and may negotiate to receive a better price than retail. In some instances, purchasers for the health care provider may be unaware of a contract and purchase a good at retail the health care provider could have bought for a lower price under a contract. In other examples, the health care provider may agree to a contract price with a vendor but the vendor may send an invoice charging a higher price due to an oversight. The analysis server 108 may monitor the invoice records and health care provider's contracts to create action items. Below are three examples.

In a first example, the analysis server 108 may review the invoice records to identify each drug or supply item being purchased and a contract corresponding to the purchase. The analysis server 108 may determine if the vendor (e.g., drug distributor, supply distributor, etc.) charged a price higher than a price specified in the contract. To correct this, the analysis server 108 may create an action item to alert an administrator of the health care provider. The analysis server 108 may also communicate an overcharge message to the supplier server 104 and/or to the distributor server 106 identifying the drug or supply item and the amount of the overcharge, and requesting a credit and/or refund for the overcharge.

In a second example, the analysis server 108 may review the invoice records to identify each drug or supply item being purchased and a contract corresponding to the purchase. The analysis server 108 may determine if the vendor (e.g., drug distributor, supply distributor, etc.) charged a price lower than a price specified in the contract. To correct this, the analysis server 108 may create an action item to alert an administrator of the health care provider. The analysis server 108 may also communicate an undercharge message to the supplier server 104 and/or to the distributor server 106 identifying the drug or supply item and the amount of the undercharge, and submitting a payment message along with account information for submitting payment to cover the undercharge.

In a third example, the analysis server 108 may review the invoice records to identify each drug or supply item being purchased, and identify any item being purchased from a non-preferred vendor. A non-preferred vendor may sell an item at a retail price where the health care provider has entered into contract with a preferred vendor to buy that same item at a contract price. In many instances, the retail price may be higher than the contract price. In response to detecting a purchase from a non-preferred vendor, the analysis server 108 may create an action item to alert a health care provider administrator about non-contract purchases. In some instances, the action item may alert the health care provider administrator if a retail price is less than the contract price such that the lower price can be used to re-negotiate the contract and/or to permit purchases outside of the contract at the lower retail price.

FIG. 8 illustrates a flow diagram of a method in accordance with example embodiments. The flow diagram may be implemented by a system or apparatus, such as, for example, analysis server 108. Each of the blocks shown in the flow diagram may be repeated one or more times, one or more of the blocks may be modified, and one or more of the blocks may be omitted. The method may be stored on a non-transitory computer readable medium as computer executable instructions. The computer executable instructions, when executed by at least one processor, may cause at least one computer or other device to perform the blocks as steps of a method one or more times. The flow diagram may begin at block 802.

In block 802, the method may include retrieving a plurality of cost of care records identifying costs to treat a plurality of patients diagnosed with a particular ailment. In an example, the analysis server 108 may retrieve cost of care records for treating a particular ailment from the CoCR database 124, and may group the cost of care records into groups based on common use of one or more drugs and/or supplies.

In block 804, the method may include processing the cost of care records for determining at least one factor for each of a plurality of treatment modalities. In an example, the analysis server 108 may process the cost of care records to determine a financial factor, a quality factor, or both for each of the treatment modalities.

In block 806, the method may include determining a performance index for each of the treatment modalities that is a weighted function of the at least one factor. In an example, the analysis server 108 may determine a performance index for each modality based on a financial factor, a quality factor, or both.

In block 808, the method may include selecting one of the treatment modalities based on the performance indices.

In block 810, the method may include automatically ordering at least one of a drug and a supply item corresponding to the selected treatment modality for delivery to a health care provider.

The method of FIG. 8 may end, may repeat one or more times, or may return to any of the preceding blocks.

Advantageously, the example embodiments may provide technical solutions to a technical challenges. For example, existing hospital systems may be technically deficient by failing to meaningfully link together patient data to enable evaluation of different treatment modalities. The example embodiments may solve this problem by importing patient, charge, and invoice data and creating cost of care records based on such data, creating performance indices for evaluating the different modalities, and ordering supplies and/or drugs based on the rankings of a treatment modality. Moreover, the example embodiments may provide a user-configurable set-up that permits health care providers to weight performance factors and to generate a composite performance index for assessing a health care provider's performance against all other or a user-defined peer set. Moreover, a user may "drill into" another anonymized health care provider's performance factors to better understand differences in inputs that drive a competitor's performance index. For example, a hospital may determine that its higher than average pharmacy costs per discharge is a result of overprescribing of a particular expensive medication or that the hospital is paying significantly higher for certain drugs as compared to similar hospitals based on size, patient mix and other variables. A health care provider may use the GUIs described herein to see average purchasing costs for specific types of drugs by NDC number. Moreover, the example embodiments may identify action items for improving upon a performance index. Clicking to resolve an action item may launch a workflow feature permitting resolution of one or more specific missed opportunities and, if appropriately resolved, would subsequently improve the performance factor and hence the performance index. Advantageously, the example embodiments may permit visibility into anonymized detailed financial, operational, clinical and resource utilization data of similar types of hospitals that have better ranked performance indices.

The example embodiments may be implemented on computers and servers such as, for example, general purpose computers that may have, among other elements, a microprocessor (such as from the Intel Corporation, AMD or Motorola); volatile and non-volatile memory; one or more mass storage devices (i.e., a hard drive); various user input devices, such as a mouse, a keyboard, or a microphone; and a video display system. The computers and servers in FIG. 1 may be running on any one of many operating systems including, but not limited to WINDOWS, UNIX, LINUX, MAC OS, or Windows (XP, VISTA, etc.). It is contemplated, however, that any suitable operating system may be used for the present invention. The computers and servers in FIG. 1 may be a cluster of web servers, which may each be LINUX based and supported by a load balancer that decides which of the cluster of web servers should process a request based upon the current request-load of the available server(s).

The computers and servers may be connected via networks, including the Internet, WAN, LAN, Wi-Fi, other computer networks (now known or invented in the future), and/or any combination of the foregoing. It should be understood by those of ordinary skill in the art having the present specification, drawings, and claims before them that networks may connect the various components over any combination of wired and wireless conduits, including copper, fiber optic, microwaves, and other forms of radio frequency, electrical and/or optical communication techniques. It should also be understood that any network may be connected to any other network in a different manner. The interconnections between computers and servers in system 100 are examples. Any device may communicate with any other device via one or more networks.

The example embodiments may include additional devices and networks beyond those disclosed. Further, the functionality described as being performed by one device may be distributed and performed by two or more devices. Multiple devices may also be combined into a single device, which may perform the functionality of the combined devices.

The various participants and elements described herein may operate one or more computer apparatuses to facilitate the functions described herein. Any of the elements in the above-described Figures, including any servers, user terminals, or databases, may use any suitable number of subsystems to facilitate the functions described herein.

Any of the software components or functions described in this application, may be implemented as software code or computer readable instructions that may be executed by at least one processor using any suitable computer language such as, for example, Java, C++, or Perl using, for example, conventional or object-oriented techniques.

The software code may be stored as a series of instructions or commands on a non-transitory computer readable medium, such as a random access memory (RAM), a read only memory (ROM), a magnetic medium such as a harddrive or a floppy disk, or an optical medium such as a CD-ROM. Any such computer readable medium may reside on or within a single computational apparatus and may be present on or within different computational apparatuses within a system or network.

It may be understood that the present invention as described above can be implemented in the form of control logic using computer software in a modular or integrated manner. Based on the disclosure and teachings provided herein, a person of ordinary skill in the art may know and appreciate other ways and/or methods to implement the present invention using hardware, software, or a combination of hardware and software.

The above description is illustrative and is not restrictive. Many variations of the invention will become apparent to those skilled in the art upon review of the disclosure. The scope of the invention should, therefore, be determined not with reference to the above description, but instead should be determined with reference to the pending claims along with their full scope or equivalents.

One or more features from any embodiment may be combined with one or more features of any other embodiment without departing from the scope of the invention. A recitation of "a", "an" or "the" is intended to mean "one or more" unless specifically indicated to the contrary. Recitation of "and/or" is intended to represent the most inclusive sense of the term unless specifically indicated to the contrary.

One or more of the elements of the present system may be claimed as means for accomplishing a particular function. Where such means-plus-function elements are used to describe certain elements of a claimed system it will be understood by those of ordinary skill in the art having the present specification, figures and claims before them, that the corresponding structure is a general purpose computer, processor, or microprocessor (as the case may be) programmed to perform the particularly recited function using functionality found in any general purpose computer without special programming and/or by implementing one or more algorithms to achieve the recited functionality. As would be understood by those of ordinary skill in the art that algorithm may be expressed within this disclosure as a mathematical formula, a flow chart, a narrative, and/or in any other manner that provides sufficient structure for those of ordinary skill in the art to implement the recited process and its equivalents.

While the present disclosure may be embodied in many different forms, the drawings and discussion are presented with the understanding that the present disclosure is an exemplification of the principles of one or more inventions and is not intended to limit any one of the inventions to the embodiments illustrated.

The present disclosure provides a solution to the long-felt need described above. In particular, systems and methods described herein may be configured to improve management of health care service providers. Further advantages and modifications of the above described system and method will readily occur to those skilled in the art. The disclosure, in its broader aspects, is therefore not limited to the specific details, representative system and methods, and illustrative examples shown and described above. Various modifications and variations can be made to the above specification without departing from the scope or spirit of the present disclosure, and it is intended that the present disclosure covers all such modifications and variations provided they come within the scope of the following claims and their equivalents.

What is claimed:
1. A computer-implemented method comprising:
serving, by a performance index engine comprising at least one first processor and at least one first memory storing computer executable instructions, a performance index graphical user interface from the performance index engine to a client computing device of a first health care provider, the client computing device comprising at least one second processor and at least one second memory;
receiving, by the performance index engine, one or more comparative profile corridors via the performance index graphical user interface, wherein the one or more comparative profile corridors include, for both the first health care provider and a plurality of second health care providers, one or more of a geographic location, a number of beds, a number of discharges in a predetermined time frame, a number of days patients spend with the first health care provider and each of the plurality of second health care providers, for the predetermined time frame, a patient revenue for the predetermined time frame, a percentage of patients on Medicare for the predetermined time frame, and a number of outpatient visits for the predetermined time frame;
determining, by the performance index engine, a set of the plurality of second health care providers that each include the one or more comparative profile corridors, wherein each member of the set of the plurality of second health care providers is a peer to the first health care provider;
retrieving, by the performance index engine, cost of care records for each member of the set of the plurality of second health care providers, wherein each cost of care record matches both the one or more comparative profile corridors and a diagnosis code for a treatment modality, the treatment modality including a combination of drugs and supplies used to treat a patient assigned the diagnosis code;
determining, by the performance index engine and using the retrieved cost of care records, a total costs per discharge for the treatment modality at both the first health care provider and each member of the set of the plurality of second health care providers;
receiving, by the performance index engine, an importance weighting for the treatment modality via the performance index graphical user interface, the importance weighting corresponding to both a financial factor and a quality factor for the treatment modality, the financial factor including the total costs per discharge for the treatment modality and the quality factor including, for patients assigned the diagnosis code for the treatment modality, one or more of an emergency room to inpatient time, a readmission rate, a mortality rate, a length of hospital stay, and a reinfection rate;
determining, by the performance index engine, a performance index for the treatment modality using the importance weighting, wherein each performance index is a weighted function of the financial factor and the quality factor; and
automatically adjusting, by a processor-executed signal received at a supplier server from an issue detector engine comprising at least one processor and at least one memory storing computer executable instructions, the combination of drugs and supplies delivered by the supplier server to treat the patient assigned the diagnosis code for the treatment modality at the first healthcare provider in response to the treatment modality having a highest performance index for at least one of the members of the set of the plurality of second health care providers, wherein the highest performance index signifies a lowest cost and a best quality outcome for one or more patients of the plurality of patients using the treatment modality, and adjusting the combination of drugs and supplies delivered by the supplier server includes modifying the supplies and one or more of a dose, quantity, and type of drugs for the treatment modality at the first healthcare provider to match the treatment modality having the highest performance index for the set of the plurality of second health care providers.

2. The method of claim 1, wherein the determining the performance index comprises aggregating data from the cost of care records to determine a statistical measure.

3. The method of claim 1, wherein the cost of care records correspond to data received from the first health care provider and the plurality of second health care providers.

4. The method of claim 1, wherein the cost of care records correspond to data received from a health care provider.

5. An apparatus comprising:
at least one processor; and
at least one memory storing computer executable instructions that, when executed, cause the apparatus at least to perform:
serving, by a performance index engine comprising at least one first processor and at least one first memory storing computer executable instructions, a performance index graphical user interface from the performance index engine to a client computing device of a first health care provider, the client computing device comprising at least one second processor and at least one second memory;
receiving, by the performance index engine, one or more comparative profile corridors via the performance index graphical user interface, wherein the one or more comparative profile corridors include, for both the first health care provider and a plurality of second health care providers, one or more of a geographic location, a number of beds, a number of discharges in a predetermined time frame, a number of days patients spend with the first health care provider and each of the plurality of second health care providers, for the predetermined time frame, a patient revenue for the predetermined time frame, a percentage of patients on Medicare for the predetermined time frame, and a number of outpatient visits for the predetermined time frame;
determining, by the performance index engine, a set of the plurality of second health care providers that each include the one or more comparative profile corridors, wherein each member of the set of the plurality of second health care providers is a peer to the first health care provider;
retrieving, by the performance index engine, cost of care records for each member of the set of the plurality of second health care providers, wherein each cost of care record matches both the one or more comparative profile corridors and a diagnosis code for a treatment modality, the treatment modality including a combination of drugs and supplies used to treat a patient assigned the diagnosis code;

determining, by the performance index engine and using the retrieved cost of care records, a total costs per discharge for the treatment modality at both the first health care provider and each member of the set of the plurality of second health care providers;

receiving, by the performance index engine, an importance weighting for the treatment modality via the performance index graphical user interface, the importance weighting corresponding to both a financial factor and a quality factor for the treatment modality, the financial factor including the total costs per discharge for the treatment modality and the quality factor including, for patients assigned the diagnosis code for the treatment modality, one or more of an emergency room to inpatient time, a readmission rate, a mortality rate, a length of hospital stay, and a reinfection rate;

determining, by the performance index engine, a performance index for the treatment modality using the importance weighting, wherein each performance index is a weighted function of the financial factor and the quality factor; and automatically adjusting, by a processor-executed signal received at a supplier server from an issue detector engine comprising at least one processor and at least one memory storing computer executable instructions, the combination of drugs and supplies delivered by the supplier server to treat the patient assigned the diagnosis code for the treatment modality at the first healthcare provider in response to the treatment modality having a highest performance index for at least one of the members of the set of the plurality of second health care providers, wherein the highest performance index signifies a lowest cost and a best quality outcome for one or more patients of the plurality of patients using the treatment modality, and adjusting the combination of drugs and supplies delivered by the supplier server includes modifying the supplies and one or more of a dose, quantity, and type of drugs for the treatment modality at the first healthcare provider to match the treatment modality having the highest performance index for the set of the plurality of second health care providers.

6. The apparatus of claim 5, wherein the determining of at least one factor for each of the treatment modalities comprises aggregating data from the cost of care records to determine a statistical measure.

7. The apparatus of claim 5, wherein the cost of care records correspond to data received from the first health care provider and the plurality of second health care providers.

8. The apparatus of claim 5, wherein the cost of care records correspond to data received from a health care provider.

9. A non-transitory computer readable medium storing computer executable instructions that, when executed, cause an apparatus at least to perform:

serving, by a performance index engine comprising at least one first processor and at least one first memory storing computer executable instructions, a performance index graphical user interface from the performance index engine to a client computing device of a first health care provider, the client computing device comprising at least one second processor and at least one second memory;

receiving, by the performance index engine, one or more comparative profile corridors via the performance index graphical user interface, wherein the one or more comparative profile corridors include, for both the first health care provider and a plurality of second health care providers, one or more of a geographic location, a number of beds, a number of discharges in a predetermined time frame, a number of days patients spend with the first health care provider and each of the plurality of second health care providers, for the predetermined time frame, a patient revenue for the predetermined time frame, a percentage of patients on Medicare for the predetermined time frame, and a number of outpatient visits for the predetermined time frame;

determining, by the performance index engine, a set of the plurality of second health care providers that each include the one or more comparative profile corridors, wherein each member of the set of the plurality of second health care providers is a peer to the first health care provider;

retrieving, by the performance index engine, cost of care records for each member of the set of the plurality of second health care providers, wherein each cost of care record matches both the one or more comparative profile corridors and a diagnosis code for a treatment modality, the treatment modality including a combination of drugs and supplies used to treat a patient assigned the diagnosis code;

determining, by the performance index engine and using the retrieved cost of care records, a total costs per discharge for the treatment modality at both the first health care provider and each member of the set of the plurality of second health care providers;

receiving, by the performance index engine, an importance weighting for the treatment modality via the performance index graphical user interface, the importance weighting corresponding to both a financial factor and a quality factor for the treatment modality, the financial factor including the total costs per discharge for the treatment modality and the quality factor including, for patients assigned the diagnosis code for the treatment modality, one or more of an emergency room to inpatient time, a readmission rate, a mortality rate, a length of hospital stay, and a reinfection rate;

determining, by the performance index engine, a performance index for the treatment modality using the importance weighting, wherein each performance index is a weighted function of the financial factor and the quality factor; and automatically adjusting, by a processor-executed signal received at a supplier server from an issue detector engine comprising at least one processor and at least one memory storing computer executable instructions, the combination of drugs and supplies delivered by the supplier server to treat the patient assigned the diagnosis code for the treatment modality at the first healthcare provider in response to the treatment modality having a highest performance index for at least one of the members of the set of the plurality of second health care providers, wherein the highest performance index signifies a lowest cost and a best quality outcome for one or more patients of the plurality of patients using the treatment modality, and adjusting the combination of drugs and supplies delivered by the supplier server includes modifying the supplies and one or more of a dose, quantity, and type of drugs for the treatment modality at the first healthcare provider to match the treatment modality having the highest performance index for the set of the plurality of second health care providers.

10. The computer readable medium of claim 9, wherein the determining of at least one factor for each of the treatment modalities comprises aggregating data from the cost of care records to determine a statistical measure.

11. The computer readable medium of claim 9, wherein the cost of care records correspond to data received from the first health care provider and the plurality of second health care providers.

12. The computer readable medium of claim 9, wherein the cost of care records correspond to data received from a health care provider.

\* \* \* \* \*